United States Patent [19]

Bendett

[11] Patent Number: 5,677,769

[45] Date of Patent: Oct. 14, 1997

[54] OPTICAL SENSOR UTILIZING RARE-EARTH-DOPED INTEGRATED-OPTIC LASERS

[75] Inventor: Mark Bendett, Ann Arbor, Mich.

[73] Assignee: Imra America, Ann Arbor, Mich.

[21] Appl. No.: 452,857

[22] Filed: May 30, 1995

[51] Int. Cl.$^6$ .................................................. G01N 21/27
[52] U.S. Cl. .............................. 356/440; 372/7; 385/12; 356/328
[58] Field of Search ............................. 356/440, 328; 372/6, 7; 385/12

[56] References Cited

U.S. PATENT DOCUMENTS

| | | | |
|---|---|---|---|
| 4,815,843 | 3/1989 | Tiefenthaler et al. | 385/12 X |
| 5,280,172 | 1/1994 | Di Bin et al. | 385/12 X |
| 5,317,576 | 5/1994 | Leonberger et al. | 372/6 |
| 5,452,084 | 9/1995 | Mitchell et al. | 356/301 |

FOREIGN PATENT DOCUMENTS 2218511  11/1989  United Kingdom .................. 356/440

*Primary Examiner*—Vincent P. McGraw
*Attorney, Agent, or Firm*—Burns, Doane, Swecker & Mathis

[57] ABSTRACT

An integrated-optic sensor includes a waveguide made from a substrate that is doped with rare-earth elements. A beam of light propagating along the waveguide excites these elements, causing them to emit light and thereby increase the total amount of light being propagated in the waveguide. The waveguide itself functions as a laser, so that any change in an optical property of an analyte material which forms a portion of the laser cavity can affect the operation of the laser. Consequently, the wavelength or power of light produced by the laser changes, in direct response to changes in the concentration of a material being sensed, and these changes are enhanced due to the inherent gain characteristics of the laser media.

15 Claims, 2 Drawing Sheets

OPTICAL SENSOR UTILIZING RARE-EARTH-DOPED INTEGRATED-OPTIC LASERS

FIELD OF THE INVENTION

The present invention is directed to sensors for detecting and/or measuring chemical or environmental conditions, and more particularly to sensors of this type which employ optical waveguides to sense a parameter of interest.

BACKGROUND OF THE INVENTION

Various types of devices can be employed to detect chemical properties of a material or environmental conditions. In one approach, of the type to which the present invention is directed, optical elements are used to detect the effect that a property of interest may have upon the transmission of light. For example, an optical fiber can be used to detect the presence of a substance of interest, as disclosed in U.S. Pat. Nos. 4,846,548; 5,280,172 and 5,268,972. Similarly, a planar waveguide can be employed for such a purpose, as disclosed, for example, in U.S. Pat. Nos. 5,071,248 and 5,262,842.

Typically, in these types of sensing devices, a material to be analyzed is incorporated into the structure of the optical waveguide. The index of refraction of the material changes in dependence upon the concentration of a substance to be detected. Since the material forms part of the structure of the sensor, a change in its index of refraction can produce in a change in the phase of a light beam that is propagating through the waveguide. Alternatively, the change in index of refraction can have an effect upon the coupling of light to or from the waveguide. These changes in the light propagation properties of the waveguide which result from changes in the index of refraction of the material are detected, to determine the concentration of the substance of interest. For example, in a sensor whose operation is based upon optical coupling effects, the changes are detected through variations in the amplitude of the transmitted light. Alternatively, 6in a sensor in which the changes in the concentration of the substance produce a phase change in the light beam, an interferometer can be employed to detect amplitude variations indicative of the substance concentration.

In operation, the changes in amplitude or phase that are measured to detect the concentration of a substance can be relatively slight. As a result, they can be difficult to accurately measure, which can lead to errors in the final results, or the need for more expensive measuring equipment.

In addition, interferometric sensors, which rely on phase changes as an indicator of detected phenomena, must be set up to operate in the relatively narrow linear range of a sine wave signal. Since the operating range of a sensor can drift due to changes in conditions such as temperature, constant calibration of the sensor is necessary, particularly if the sensor operates over a large dynamic range. Furthermore, these types of sensors require a mechanically stable operating environment, since any vibration or the like can disturb the phase shift measurement.

It is desirable to provide an integrated optic sensor which produces an output that is sufficiently large to be easily measured, and thereby produce more accurate results without requiring extensive calibration or a highly controlled environment.

SUMMARY OF THE INVENTION

In accordance with the present invention, these objectives are achieved by means of an integrated-optic sensor in which the waveguide itself functions as a laser, and inherently produces optical gain. This result is achieved by constructing the waveguide from a substrate that is doped with rare-earth elements. A beam of light propagating along the waveguide excites these elements, causing them to emit light and thereby increase the total amount of light being propagated in the waveguide. As a result, any changes in the light transmission properties of the waveguide that are effected by the material being analyzed are amplified, resulting in a sensor with higher sensitivity.

Furthermore, since the waveguide itself functions as a laser, any change in a property of an analyte material which forms a portion of the laser cavity can affect the operation of the laser. For example, a change in the analyte's index of refraction results in an effective change in the length of the waveguide's lasing cavity. Consequently, the wavelength of light produced by the laser changes correspondingly. These changes in wavelength can be directly detected, to provide a simpler and less expensive sensor than those which operate on the principle of detecting phase changes. Alternatively, the output power of the lasing medium can be measured to identify any changes which have occurred.

The foregoing features of the invention, as well as the advantages provided thereby, are described in greater detail hereinafter with reference to preferred embodiments illustrated in the accompanying drawings.

DETAILED DESCRIPTION

In general, an integrated optical sensor of the type provided by the present invention can be employed to detect a wide variety of chemical properties and/or environmental conditions. To facilitate an understanding of the invention and its practical applications, it is described hereinafter with reference to a specific embodiment, in which the concentration of a substance of interest is to be measured. In the described embodiment, the substance of interest is incorporated into an analyte material whose index of refraction changes in response to the concentration of the substance. It will be appreciated, however, that this is not the only practical application of the invention. For example, a substance whose concentration is being measured need not be actually incorporated within the analyte. Rather, the analyte merely needs to function such that one of its optical properties changes in response to variations in a parameter of interest. Thus, for example, in the sensing of environmental conditions, the optical transparency of the analyte might change in response to the amount of a particular substance in the air, such as water vapor, carbon dioxide, nitrous oxide, or the like.

Figure 1:
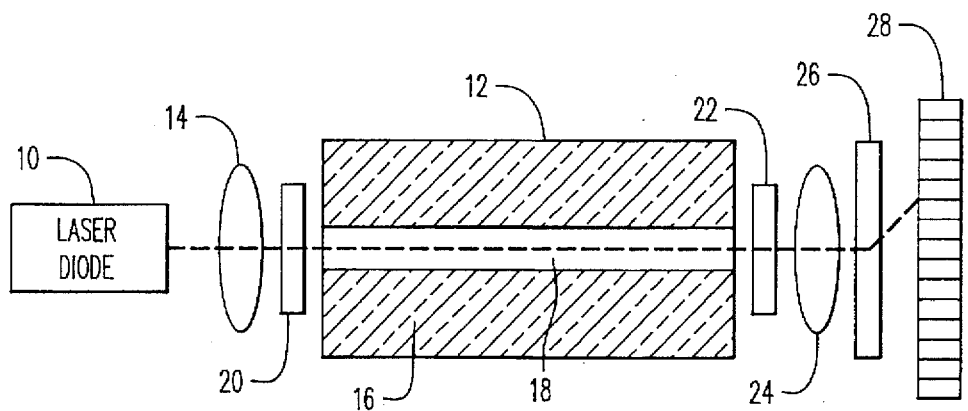
FIG. 1 is a schematic diagram of an embodiment of an optical sensor which employs the principles of the present invention.

Referring to FIG. 1, one embodiment of an integrated optic sensor which incorporates the principles of the present invention is shown in schematic form. The sensor includes a laser diode 10 which emits a beam of light at an appropriate wavelength, for example 980 nm. An output beam from the laser diode is coupled into an integrated optic device 12 by means of a suitable coupling system 14, such as a lens or an optical fiber. The optic device 12 comprises a suitable substrate 16 which has a light conducting channel 18 that forms a waveguide. Preferably, the substrate 16 is made of silica glass that is doped with a rare-earth element, for example erbium or neodymium, and the channel 18 is formed by means of ion exchange. For detailed information regarding the formation of a waveguide channel in a doped silica glass substrate by means of ion exchange, reference is made to Sanford et al, Optics Letters, Volume 15, p. 366 (1990) and Sanford et al "Y-branch waveguide glass laser and amplifier", Optics Letters, Volume 16, No. 15, Aug. 1, 1991, pp. 1168–1170, the disclosures of which are incorporated herein by reference.

When the output beam from the laser diode 10 is coupled into the device 12, it excites the rare-earth-dopants in the channel 18, causing them to emit light. A narrow band, high reflectivity mirror 20 is located at the input end of the waveguide channel 18, and another mirror 22 is disposed at the output end of the channel. These mirrors can be discrete elements, as shown, or coatings that are deposited on the ends of the optic device. The light which is emitted by the rare-earth-dopants is reflected by these mirrors, which causes the optic structure to lase.

The laser light that is generated in this manner is coupled out of the waveguide by the mirror 22, and passes through collimating optics 24 and a refractive element 26. The refractive element 26 causes the beam of light emitted by the laser waveguide to bend at an angle which is dependent upon its wavelength. A multi-element photodetector 28 senses the spatial position of the displaced light beam, to thereby provide an indication of its wavelength. The photodetector 28 can be a charge coupled device, a photodiode array, or a position-sensitive diode, for example.

As discussed in greater detail with reference to the embodiments of FIGS. 2–4, an analyte material (not shown in FIG. 1) is in contact with the light guiding channel 18. For example, the material can be placed on the surface of the waveguide, i.e. over the channel, or it can be physically incorporated into the structure of the channel. The analyte material has at least one optical property that is sensitive to a specific chemical or biological species of interest. For example, as the concentration of the species changes, the index of refraction of the analyte material can undergo a corresponding change. Since the analyte material is in optical contact with the channel 18, a change in its index of refraction produces a corresponding change in the effective length of the laser cavity. As a result, the wavelength of the light emitted by the integrated optic device 12 will change. This change in wavelength is detected by the photodetector 28, to thereby provide an indication of the concentration of the substance to which the analyte material is sensitive, relative to a known value.

The specific analyte material that is employed in the sensor does not form part of the invention, per se. Rather, it will depend upon the particular condition that is to be sensed. Various chemoresponsive materials that are sensitive to the presence of different substances are well known, and therefore are not listed herein. Particular examples of such are disclosed, for instance, in U.S. Pat. Nos. 5,212,099; 5,071,248 and 5,173,747.

Figure 2:
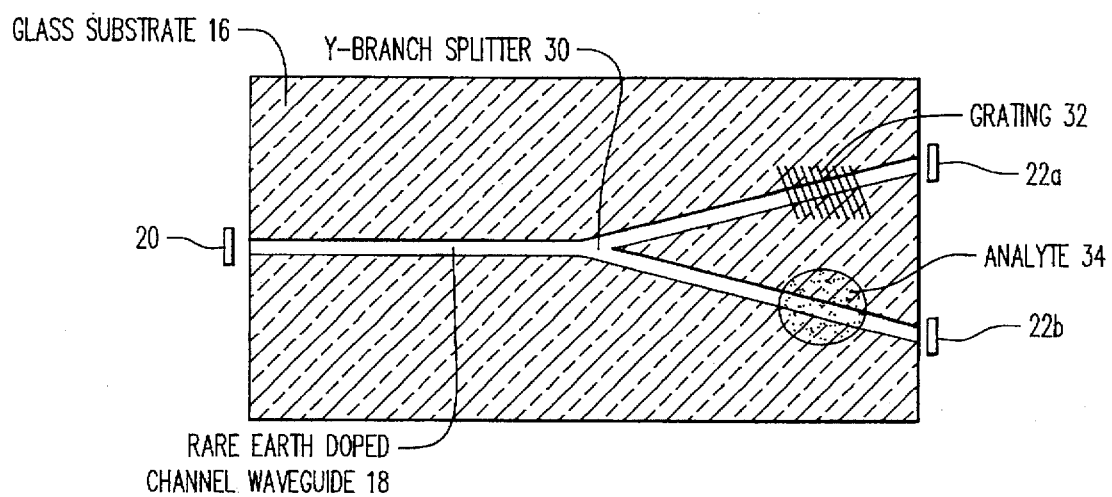
FIG. 2 is an illustration of one embodiment of a laser waveguide according to the present invention.
Figure 3:
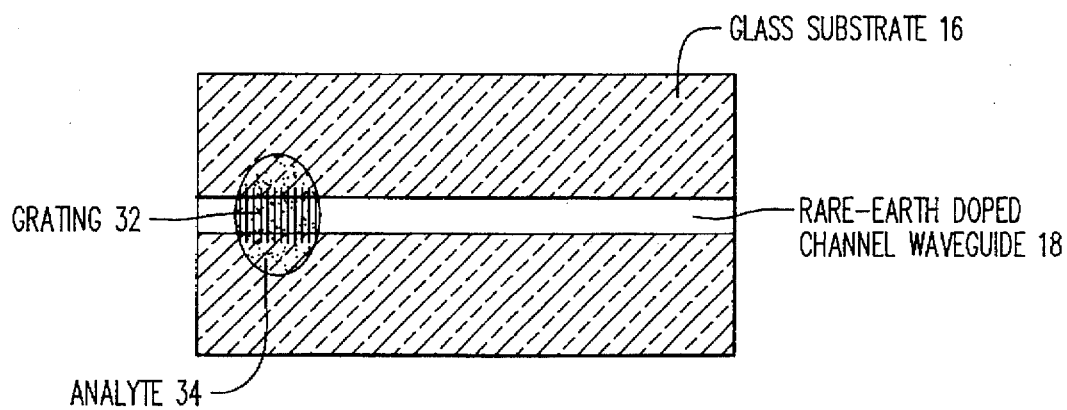
FIG. 3 is an illustration of a second embodiment of a waveguide according to the present invention.

Specific embodiments of an integrated optic device 12 that can be employed in the present invention are illustrated in FIGS. 2–4. These various embodiments illustrate different modes of interaction that can occur between the laser light within the waveguide and the analyte material. Referring to FIG. 2, in one embodiment the waveguide can include a Y-branch splitter 30. The light beam from the laser diode 10 that is coupled into the waveguide channel 18 is separated into two branches when it reaches the splitter. One branch contains an optical grating 32, which functions to define the initial emission wavelength of the laser and its linewidth. An analyte material 34 is placed on the surface of the other branch. Reflective mirrors 22a and 22b are respectively located at the output ends of each of the two branches, to thereby produce the lasing function in concert with a mirror 20 at the input end of the waveguide. Light reflected by the two mirrors 22a, 22b is coupled at the Y-branch splitter 30, and defines the output wavelength of the laser. The laser light generated within the laser waveguide is coupled out through the mirror 22a, and its wavelength is sensed by the photodetector. Since changes in the index of refraction of the analyte material 34 result in corresponding changes in the effective length of its associated branch of the laser cavity, the wavelength of the light that ultimately results from the coupling effect of the splitter will also vary, and can be detected.

This type of operation provides a number of advantages over previously known integrated optics sensors. By its very nature, a laser medium exhibits optical gain with respect to the light energy being propagated through the waveguide. As such, any effects that a change in the index of refraction of the analyte have on the light propagation will be amplified in the resulting output signal, thereby increasing the overall sensitivity of the detector. In addition, since the wavelength of the output beam, rather than the phase of the light, is the parameter being measured, mechanical vibration of the sensor does not have an adverse effect on the measurement. As such, less stringent control of the operating environment is required.

Furthermore, this type of structure does not require continual calibration. The initial output signal of the sensor, e.g. the wavelength of the light, provides a reference point, regardless of its value. Any subsequent changes in the wavelength can be readily measured against the original signal, to provide an indication of the change in the measured condition, without any need to calibrate the signal.

As a further advantage, the structure can be readily modified to provide desired types of output signals. For example, if the effects of a specific analyte are enhanced for light within a particular frequency range, the rare earth element that is used to dope the waveguide structure can be selected to provide light within that range. As such, the structure of the sensor can be optimized to sense different conditions.

In the embodiment of FIG. 2, only the evanescent tail of the optical mode contained in the waveguide, i.e., that portion of the optical mode which is at the boundary of the channel 18, interacts with the analyte. A second mode of interaction between the laser light and the analyte occurs in the embodiment illustrated in FIG. 3. Referring thereto, this embodiment comprises a single linear channel 18. An optical grating 32 is disposed on the channel, and the analyte material 34 is incorporated within the structure of the grating. For example, the analyte material itself can constitute the grating, i.e., strips of the analyte are disposed on the surface of the substrate. Alternatively, the analyte can be in contact with a grating that is integrally formed in the glass structure. In the operation of this embodiment, changes in wavelength are produced by changes in the feedback ratio of the grating on top of the laser, which are a result of variations in the index of refraction of the analyte due to its sensitivity to the substance being detected. The grating is the primary feedback mechanism which determines the wavelength and linewidth of the output beam from the laser. As a result, relatively small changes in the feedback mechanism, produced by changes in the index of refraction of the analyte, can induce large effects in the output wavelength of the laser, thereby providing a highly sensitive structure.

Figure 4A:
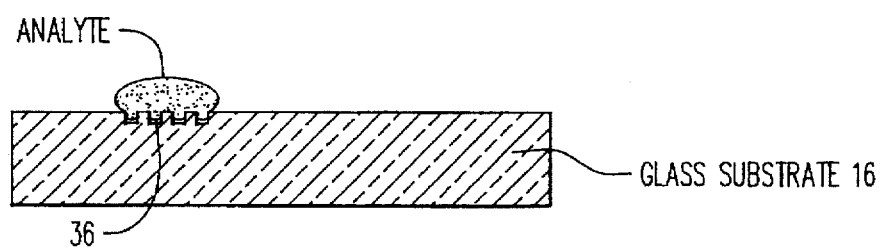
FIGS. 4a and 4b are side and top views of a third embodiment of a waveguide incorporating the principles of the present invention.
Figure 4B:
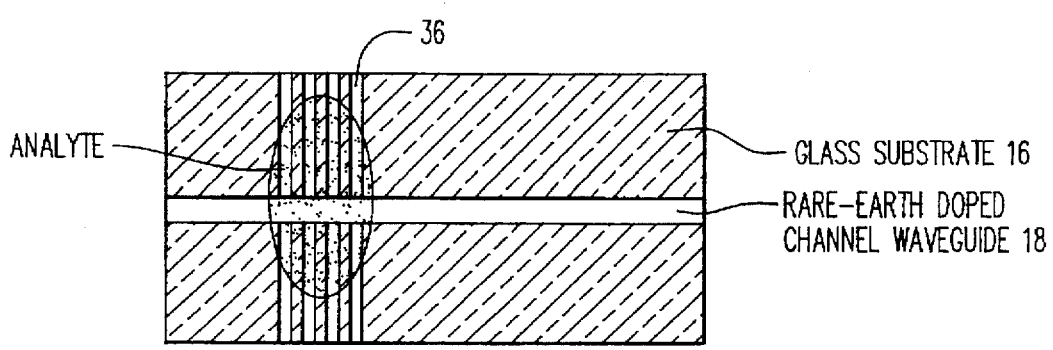

A third embodiment of the laser waveguide is illustrated in FIGS. 4a and 4b, which respectively comprise a side view and a top view of the structure. The embodiments of FIGS. 2 and 3 rely upon changes in the index of refraction to induce changes in the output wavelength of the laser waveguide. In the embodiment of FIG. 2, only the evanescent tail of the optical mode contained in the waveguide, i.e., that portion of the optical mode which is at the boundary of the channel 18, interacts with the analyte. In the embodiment of FIGS. 4a and 4b, however, the analyte is incorporated into the structure of the waveguide channel, so that the entire optical mode can interact with it, rather than merely the evanescent tail. In this embodiment, grooves 36 are formed in the substrate, transverse to the direction of propagation of the light beam through the waveguide channel. Preferably, these grooves are perpendicular to the channel itself. The analyte is disposed within these channels, so that it is present inside the laser cavity. To avoid significant disturbances of the laser cavity, the widths of the channels should be relatively small, on the order of a few microns. In operation, since the analyte is disposed within the laser cavity, changes in its optical properties will affect the entire optical mode that propagates through the channel 18. While the total length over which the optical mode interacts with the analyte may be relatively short in this embodiment, the effect of the analyte per unit length can be expected to be significantly greater. This embodiment is most preferably employed with analytes whose optical transparency varies as a function of the concentration of the substance being detected. With this embodiment, it may be preferable to measure the output power of the emerging light beam, e.g. the amount of attenuation, rather than its wavelength, to detect changes in the sensed condition.

From the foregoing, it can be seen that the present invention provides an integrated-optic sensor in which the waveguide itself functions as a laser, and a change in the analyte perturbs the laser structure, to cause a change in wavelength or output power. The function of the analyte in the laser can take the form of interaction with the evanescent tail of the laser light, modification of a grating feedback ratio, or direct interaction with the entire optical mode.

Due to the inherent gain characteristics of the laser structure, a small perturbation that is induced in the waveguide by changes in the analyte is significantly amplified in the output light beam. As a result, much greater sensitivity to changes is achieved, relative to sensors which lack such inherent gain. Furthermore, since the sensor relies on changes in wavelength or power as an indicator, rather than phase shift, the detection of such changes can be done in a simpler and less expensive manner.

It will be appreciated by those of ordinary skill in the art that the present invention can be embodied in other specific forms without departing from the spirit or essential characteristics thereof. The presently disclosed embodiments are considered in all respects to be illustrative and not restrictive. The scope of the invention is indicated by the appended claims rather than the foregoing description, and all changes that come within the meaning and range of equivalence thereof are intended to be embraced therein.

What is claimed is:

1. An optical sensor for detecting chemical and/or environmental conditions, comprising:
   a source which generates a beam of coherent light;
   an integrated optic waveguide for receiving and propagating said beam of light, said waveguide comprising a substrate having a channel that is doped with a rare-earth element and reflectors located at opposite ends of said channel to thereby form a laser cavity;
   an analyte material in contact with said waveguide channel, said analyte having an optical property that changes in response to variations in the condition being detected, to thereby vary at least one of the wavelength and power of light generated in said laser cavity; and
   a detector for measuring changes in the wavelength or power of said light generated in said laser cavity.

2. The sensor of claim 1 wherein said substrate is glass.

3. The sensor of claim 2 wherein said glass is doped with a rare-earth element.

4. The sensor of claim 1 wherein said optical property is the index of refraction of the analyte material.

5. The sensor of claim 4 further including an optical grating disposed on said waveguide channel.

6. The sensor of claim 5 wherein said optical grating is integrally formed in said integrated optic waveguide, and said analyte material is located on said optical grating.

7. The sensor of claim 5 wherein said optical grating is formed by said analyte material.

8. The sensor of claim 5 wherein said channel is Y-shaped to thereby form two branches which are optically coupled, and wherein said grating is disposed on one of said branches and said analyte material is disposed on the other branch.

9. The sensor of claim 1 wherein said property is the optical transparency of the analyte material.

10. The sensor of claim 9, further including grooves formed in said channel and oriented in a direction transverse to the direction of propagation of said beam of light, and wherein said analyte material is disposed in said grooves.

11. An optical sensor for detecting chemical and/or environmental conditions, comprising:
    a source which generates a beam of coherent light;
    an integrated optic waveguide for receiving and propagating said beam of light, said waveguide comprising a substrate having a channel that is Y-shaped to thereby form two branches which are optically coupled, and being doped with a rare-earth element;
    reflectors located at the ends of each branch in said channel to thereby form a laser cavity;
    a grating disposed on one of said branches;
    an analyte material disposed on the other of said branches, said analyte having an optical property that changes in response to variations in the condition being detected, to thereby vary at least one of the wavelength and power of light generated in said laser cavity; and
    a detector for measuring changes in the wavelength or power of said light generated in said laser cavity.

12. An optical sensor for detecting chemical and/or environmental conditions, comprising:
    a source which generates a beam of coherent light;
    an integrated optic waveguide for receiving and propagating said beam of light, said waveguide comprising a substrate having a channel that is doped with a rare-earth element and reflectors located at opposite ends of said channel to thereby form a laser cavity;
    grooves formed in said channel and oriented in a direction transverse to the direction of propagation of said beam of light an analyte material disposed in said grooves, said analyte having an optical property that changes in response to variations in the condition being detected, to thereby vary at least one of the wavelength and power of light generated in said laser cavity; and a detector for measuring changes in the wavelength or power of said light generated in said laser cavity.

13. An optical sensor for detecting chemical and/or environmental conditions, comprising:

a source which generates a beam of coherent light;

an integrated optic waveguide for receiving and propagating said beam of light, said waveguide comprising a substrate having a channel that is doped with a rare-earth element and reflectors located at opposite ends of said channel to thereby form a laser cavity;

an optical grating disposed on said waveguide channel;

an analyte material optically coupled with said optical grating, said analyte having an optical property that changes in response to variations in the condition being detected, to thereby vary at least one of the wavelength and power of light generated in said laser cavity; and a detector for measuring changes in the wavelength or power of said light generated in said laser cavity.

14. The optical sensor of claim 13 wherein said optical grating is integrally formed in said integrated optic waveguide, and said analyte material is located on said optical grating.

15. The optical sensor of claim 13 wherein said optical grating is formed by said analyte material.

* * * * *